United States Patent
Oguma et al.

[11] Patent Number: 5,238,825
[45] Date of Patent: Aug. 24, 1993

[54] PREPARATION AND USE OF A CYCLODEXTRINASE FOR PREPARING MALTOOLIGOSACCHARIDES

[75] Inventors: Tetsuya Oguma; Mamoru Kikuchi; Kiyoshi Mizusawa; Shoichi Tokutake; Nobuyuki Yamaji, all of Noda, Japan

[73] Assignee: Kikkoman Corporation, Noda, Japan

[21] Appl. No.: 835,592

[22] Filed: Feb. 14, 1992

Related U.S. Application Data

[62] Division of Ser. No. 533,856, Jun. 6, 1990, Pat. No. 5,110,734.

[30] Foreign Application Priority Data

Jun. 12, 1989 [JP] Japan .................. 1-146891
Jun. 16, 1989 [JP] Japan .................. 1-152257

[51] Int. Cl.$^5$ .............................. C12P 19/04
[52] U.S. Cl. ............................ 435/101; 435/97
[58] Field of Search ......................... 435/97, 101

[56] References Cited

U.S. PATENT DOCUMENTS 5,008,195  4/1991  Allenza et al. .................. 435/193

OTHER PUBLICATIONS

Methods in Enzymology, vol. 5, pp. 148–155 (1962).
Archives of Biochemistry and Biophysics, vol. 155, pp. 290–298 (1973).
Agric. Biol. Chem., vol. 47 (7), pp. 1441–1447 (1983).
Biochemistry, vol. 7, No. 1, pp. 121–124 (1968).
Nomoto et al., Agric. Biol. Chem., 50(11), pp. 2701–2707, (1986).
Kitahata et al., Chemical Abstracts, vol. 102, #21, p. 266, #181446+.

*Primary Examiner*—Ronald W. Griffin
*Assistant Examiner*—Pamela S. Webber
*Attorney, Agent, or Firm*—Banner, Birch, McKie & Beckett

[57] ABSTRACT

The present invention relates to the preparation of a cylodextrinase having specific physicochemical characteristics relating to action, substrate specificities, optimum pH, stable pH, inhibition, activation and molecular weight by culturing a specified microorganism belonging to the genus Bacillus, and also provides a process for preparing maltooligosaccharides by using the present enzyme on cylodextrins.

1 Claim, 10 Drawing Sheets

1: GLUCOSE  2: MALTOSE
3: MALTOTRIOSE  4: MALTOTETRAOSE
5: MALTOPENTAOSE  6: MALTOHEXAOSE
7: MALTOHEPTAOSE

PREPARATION AND USE OF A CYCLODEXTRINASE FOR PREPARING MALTOOLIGOSACCHARIDES

This application is a division of application Ser. No. 07/533,856, filed Jun. 6, 1990, now U.S. Pat. No. 5,110,734.

BACKGROUND OF THE INVENTION

1. Field of the Invention

This invention relates to a cyclodextrinase, its preparation process, and a process for preparing maltooligosaccharides using said enzyme.

2. Description of the Prior Art

Few reports are available on the enzyme cyclodextrinase (which is also called cyclomaltodextrinase EC 3.2.1.54). To the present inventors' knowledge, there are merely known the enzyme produced by a microorganism *Bacillus macerans* (Biochemistry, Vol. 7, pp. 121-124, 1968), and by a microorganism *Bacillus coagulans* (Agric. Biol. Chem., Vol. 47, pp. 1441-1447, 1983).

Regarding preparation of maltooligosaccharides, a process is known in which the desired oligosaccharides are produced from starch, etc., under the action of amylases capable of producing specified oligosaccharides ranging from glucose to maltohexaose (Arch. Biochem. Biophys., Vol. 155, pp. 290-298, 1973).

There are also known a method for producing such maltooligosaccharides as maltohexaose and higher-order ones (i.e., those with more than 6 glucoside-bonded monosaccharide molecules) by using cyclodextrins as the starting material and cleaving them by acid hydrolysis (Japanese Patent Kokai No. 191690/86), and a method for producing such oligosaccharides as maltoheptaose and higher-order ones, in which the coupling reaction of cyclodextrin and monosaccharide or cyclodextrin and oligosaccharide is catalyzed by using cyclodextrin glucanotransferase (E.C. 2.4.1.19) which is produced by *Bacillus macerans* (Methods in Enzymology, Vol. 5, pp. 148-155, 1962).

Maltooligosaccharides are not only useful as a substrate for the assay of serum amylase, with their demand for such use increasing, but also their wide application to pharmaceuticals, chemicals and foods, for example as base material of nutritine agent, excipients, bulk fillers, etc., is expected.

However, no amylase is yet known which is capable of specifically producing maltooligosaccharides having a greater number of glucoside-bonded monosaccharide molecules than maltoheptaose from starch, nor is established any efficient method for producing such oligosaccharides according to an enzymatic process using starch as the starting material.

In production of oligosaccharides such as maltohexaose and higher-order ones by using cyclodextrins as the starting material, the method of acid hydrolysis has the problem that a large amount of by-products are generated to excessively reduce the yield of the desired hydrolyzate. Also, the enzymatic method using cyclodextrin glucanotransferase involves the problem that a substantial amount of unreacted cyclodextrin remains in the reaction solution as it is necessary to control the rate of reaction for converting cyclodextrin to the objective product at a low level because of possible decomposition of the product itself or increased build-up of by-products by a coupling reaction between the product and cyclodextrin with the progress of the reaction, and therefore purification of the product becomes difficult.

SUMMARY OF THE INVENTION

The present inventors have screened out microorganisms capable of producing cyclodextrinase from soil and, as a result of many tests and studies thereof, found that a strain belonging to the genus Bacillus can produce a cyclodextrinase which is completely different from hitherto known ones. The present invention was attained on the basis of this striking finding.

The present inventors have made further researches with a view to enabling obtainment of high-purity maltooligomsaccharides quickly and efficiently to sweep away the prior art problems mentioned above, and consequently reached the remarkable finding that when said cyclodextrinase is catalytically acted to cyclodextrin, a maltooligosaccharide corresponding to the polymerization degree of glucose of cyclodextrin is produced and accumulated in a high yield. This finding represents another aspect of the present invention.

DESCRIPTION OF THE PREFERRED EMBODIMENTS

The present invention provides a cyclodextrinase having the following specific physicochemical properties:

(1) Action

The cyclodextrinase provided according to this invention has the action to cause cleavage of cyclodextrin to produce an oligosaccharide corresponding to the polymerization degree of glucose of cyclodextrin.

(2) Substrate Specificity

The hydrolysis rate or affinity for cyclodextrin is greater than that of polysaccharides or linear maltooligosaccharides with the same polymerization degree of glucose as cyclodextrin.

(3) Optimum pH and Stable pH Range

The optimum pH is around 8.0 when $\beta$-cyclodextrin is used as substrate. The stable pH range is 5.5-9.5.

(4) Optimum Working Temperature

The optimum working temperature is around 40° C.

(5) Conditions of Inactivation

The cyclodextrinase of this invention is substantially inactivated by a treatment at a temperature of 50° C. or more for a period of 15 minutes.

(6) Inhibition and Activation

The enzyme of this invention is inhibited 90% or more by $Hg^{2+}$, $Cu^{2+}$, $Zn^{2+}$, $Ni^{2+}$ and $Fe^{2+}$ and activated 10–30% by $Ca^{2+}$ and $Mg^{2+}$.

(7) Molecular Weight

The molecular weight of the cyclodextrinase according to this invention is 144,000 when measured by gel filtration method and 72,000 when measured by SDS PAGE method.

The present invention also provides a process for producing the cyclodextrinase characterized in that a microorganism *Bacillus sphaericus* E-244 (FERM BP-2458) having the ability to produce the cyclodextrinase is cultured in a medium to yield and accumulate said cyclodextrinase, and this enzyme is collected from the culture.

It is further envisaged in this invention to provide a process for producing maltooligosaccharides characterized in that the cyclodextrinase having the above specified physicochemical properties is catalytically acted to cyclodextrins.

The present invention will be described in detail below.

At first, the cyclodextrinase of this invention will be described from the aspect of its physicochemical properties.

(1) Action

It acts to cyclodextrins and produces maltooligosaccharides corresponding to the polymerization degree of glucose of the cyclodextrins.

(2) Substrate Specificity

The substrate specificity of the present cyclodextrinase is such as shown in Table 1. The reaction rate parameters of the enzyme of this invention (hereinafter referred to as present enzyme) in relation to cyclodextrins and maltooligosaccharides are as shown in Table 2.

TABLE 1

| Substrate | Conc. | Relative hydrolysis rate (%) |
| --- | --- | --- |
| $\beta$-cyclodextrin | 2 mM | 100 |
| $\alpha$-cyclodextrin | 2 mM | 44 |
| Maltopentaose | 2 mM | 49 |
| Maltohexaose | 2 mM | 43 |
| Maltoheptaose | 2 mM | 66 |
| Amylose ($G_{18}$) | 0.1% | 44 |
| Amylose ($G_{99}$) | 0.1% | 3.7 |
| Amylopectin | 0.1% | 0.7 |
| Starch | 0.1% | 2.9 |
| Pullulan | 0.1% | 1.5 |
| Dextran | 0.1% | 11 |

TABLE 2

| Substrate | Km (mM) | Vmax | Vmax/Km | Relative value |
| --- | --- | --- | --- | --- |
| $\beta$-cyclodextrin | 0.38 | 0.110 | 0.2895 | 1.00 |
| $\alpha$-cyclodextrin | 0.71 | 0.074 | 0.1042 | 0.36 |
| $\gamma$-cyclodextrin | 1.43 | 0.039 | 0.0273 | 0.09 |
| Maltotetraose | 1.54 | 0.067 | 0.0435 | 0.15 |
| Maltopentaose | 0.95 | 0.073 | 0.0768 | 0.27 |
| Maltohexaose | 1.11 | 0.075 | 0.0676 | 0.23 |
| Maltoheptaose | 0.69 | 0.060 | 0.0870 | 0.30 |

(3) Optimum pH and Stable pH Range

The optimum pH is as shown in FIG. 1. It is around 8.0 when 1% $\beta$-cyclodextrin is used as substrate. The stable pH range is as shown in FIG. 2. It was determined by measuring the residual activity after a 24-hour treatment at 25° C. at each specified pH. As seen from FIG. 2, the stable pH range is 5.5–9.5.

(4) Determination of Potencies

500 $\mu$l of a 2% solution of $\beta$-cyclodextrin and 500 $\mu$l of a 100 mM phosphate buffer solution (pH 7.5) containing a proper amount of the present enzyme were mixed and reacted at 40° C. for an appropriate period of time, after which the solution was boiled for 10 minutes to terminate the reaction and the resultantly produced maltoheptaose was determined by high performance liquid chromatography (hereinafter referred to as HPLC). When the amount of the enzyme was small, the reducing power of the enzyme was determined according to Nelson-Somogyi's method, with glucose as standard.

As for the enzymic unit of the present enzyme, the quantity of the enzyme which can produce 1 micromole of maltoheptaose in one minute was defined as one unit.

(5) Optimum Working Temperature

As seen from FIG. 3, the optimum working temperature of the present enzyme is around 40° C.

(6) Temperature and Other Conditions for Inactivation

As seen from FIG. 4, the present enzyme maintained stable activity at a temperature of up to 45° C. in a 15-minute treatment in a 100 mM phosphate buffer solution (pH 7.5) but was inactivated at a temperature of 50° C. or more.

(7) Inhibition and Activation

The results of investigation of the influence of metal ions on the activity of the present enzyme are shown in Table 3. As seen from the table, the present enzyme was inhibited almost 100% by $Hg^{2+}$, $Cu^{2+}$, $Zn^{2+}$, $Ni^{2+}$ and $Fe^{2+}$, which are divalent metal ions, and activated approximately 10–30% by $Ca^{2+}$ and $Mg^{2+}$.

TABLE 3

| Ions added (final conc.: 1 mM) | Residual activity (%) |
| --- | --- |
| None | 100 |
| $Mg^{2+}$ | 111.3 |
| $Ca^{2+}$ | 138.2 |
| $Mn^{2+}$ | 59.3 |
| $Fe^{3+}$ | 41.6 |
| $Fe^{2+}$ | 4.6 |
| $Cu^{2+}$ | 2.8 |
| $Ni^{2+}$ | 0.9 |
| $Zn^{2+}$ | 0.0 |
| $Hg^{2+}$ | 0.0 |

(8) Purification Method

Described in the Examples given later.

(9) Molecular Weight

The present enzyme shows a molecular weight of 72,000 when measured according to SDS PAGE method and 144,000 when measured according to gel filtration method, so that this enzyme is a dimer consisting of subunits with a molecular weight of 72,000.

The differences in physicochemical properties between the present enzyme and the known cyclodextrinase are shown in Table 4.

TABLE 4

| Origin | Bacillus sphaericus (present invention) | | Basillus macerans (microogranism shown in prior literature) | Bacillus coagulans (microorganism shown in prior literature) |
|---|---|---|---|---|
| Optimum pH | 8.0 | | 6.2-6.4 | 6.2 |
| Molecular weight | 144000 | | 23S | 62000 |
| Km value | α-cyclodextrin | 0.71 mM | 2.62 mM | 10.0 mM |
| | β-cyclodextrin | 0.38 mM | 2.65 mM | 2.8 mM |
| | Maltohexaose | 1.11 mM | No mention | 1.5 mM |
| | Maltoheptaose | 0.69 mM | No mention | No mention |

As described above, the enzyme provided in accordance with this invention differs in properties from the known cyclodextrinase and can be notably distinguished from them in that the present enzyme acts to cyclodextrins in an optimal way.

Use of the present enzyme enables efficient industrial production of maltooligosaccharides from cyclodextrins, said maltoologosaccharides having chain length depending on the polymerization degree of glucose of cyclodextrin.

A process for preparing the enzyme according to this invention is described below.

The microorganism used in the process for producing the present enzyme may be selected from those microorganisms which belong to the genus Bacillus and are capable of producing the present enzyme. A typical example of such microorganisms is *Bacillus sphaericus* E-244 strain. This strain is a wild type strain obtained from soil and shows the following bacteriological properties.

Bacteriological properties of Bacillus sphaericus E-244 strain (a) Morphology
  (1) Shape and size of cell: rod, 0.6-0.8×1.6-4.0 microns
  (2) Polymorphism of cell: not observed
  (3) Motility: motile with peritrichate flagella
  (4) Spore: present
    Sporangium: evaginated
    Size: 0.8-0.9×1.1-1.2 microns
    Shape: elliptic
    Position: subterminal
  (5) Gram-stain: positive
  (6) Acid fastness: negative
(b) Growth in media
  (1) Broth agar plate culture
    Colorless diffusible colonies are formed.
    Colonies are flat and smooth at the periphery.
    No pigment is formed.
  (2) Broth agar slant culture
    Mycelial mat is flat and smooth at the periphery.
    No formation of pigment occurs.
  (3) Broth liquid culture
    Growth of bacterium is observed in the whole medium, but no precipitate is seen.
  (4) Broth gelatin stab culture
    Growth of bacterium is noted only in the upper part of the medium. No liquefaction is observed.
  (5) Litmus milk
    No coagulation takes place nor is formation of acids and alkalis seen.
(c) Physiological properties
  (1) Reduction of nitrates: not observed
  (2) Denitrification reaction: does not occur
  (3) MR test: negative
  (4) VP test: negative
  (5) Formation of indole: not seen
  (6) Formation of hydrogen sulfide: not seen
  (7) Hydrolysis of starch: not caused
  (8) Utilization of citric acid: no
  (9) Utilization of inorganic nitrogen source: no
  (10) Formation of pigment: not seen
  (11) Urease: negative
  (12) Oxydase: positive
  (13) Catalase: positive
  (14) Temperature range for growth: 13°-38° C.
    pH range for growth: 6-10.5
  (15) Behavior against oxygen: aerobic
  (16) O-F test: negative (no formation of acid is seen)
  (17) Behavior against saccharides
    No formation of acid and gas from L-arabinose, D-xylose, D-glucose, d-mannose, D-fructose, D-galactose, maltose, sucrose, lactose, trehalose, D-sorbitol, D-mannitol, inositol, glycerin and starch is seen.
(d) Deamination reaction of phenylalanine: positive Being confirmed to be a gram-positive bacillus which forms the spores, the *Bacillus sphaericus* E-244 strain was identified as a bacterium belonging to the genus Bacillus. Further, in the light of the facts that no formation of acid and gas from saccharides is seen, that pH of VP broth is 7.0 or above, and that there is observed a deamination reaction of phenylalanine, the subject strain was determined to be a bacterium belonging to the species sphaericus of the genus Bacillus with reference to Bergey's Manual of Systematic Bacteriology, Vol. 2, 1984.

*Bacillus sphaericus* E-244 strain is deposited at the Fermentation Research Institute of Agency of Industrial Science and Technology under FERM BP-2458.

Cultivation of the strain can be, in principle, accomplished by the same method as employed for aerobic culture of ordinary microorganisms, but usually shaking culture with a liquid medium or aerated spinner culture is used. As the culture medium, there is used the one containing an appropriate nitrogen source, carbon source, vitamins, minerals and other commonly employed substances as well as cyclodextrin which is an inductive substrate for the present enzyme. Regarding pH of the medium, any appropriate pH for growth of the present bacterium may be used, but usually a pH range of 6-8 is preferred.

As for the culturing conditions, the subject bacterium is cultured, for example, by shaking culture or aerated spinner culture usually at a temperature of 20°-40° C. for a period of from 16 hours to 4 days.

The culture thus obtained is, for example, subjected to the following enzyme collecting operations to give a purified preparation of the present enzyme. That is, for obtaining the enzyme from said culture, the latter is centrifuged or subjected to diaphragmatic concentration or other means to gather the bacterial cells and these cells are crushed by a supersonic treatment, a treatment with a surfactant or other operations, and the residual cells are removed by centrifugation or other suitable means to obtain a crude enzyme solution. This crude enzyme solution is then subjected to a proper combination of column chromatographic treatments such as ion exchange chromatography, hydrophobic chromatography, gel filtration, etc. to give a purified product of the present enzyme.

A process for preparing maltooligosaccharides is described below.

The cyclodextrinase described above is catalytically acted to cyclodextrins, and the maltooligosaccharides corresponding to the polymerization degree of glucose of cyclodextrins are obtained from the reaction solution (for example, there can be obtained maltohexaose from α-cyclodextrin, maltoheptaose from β-cyclodextrin and maltooctaose from γ-cyclodextrin).

In this invention, it is possible to use any known types of cyclodextrin and their derivatives including branched and modified ones as far as they have a cyclodextrin skeleton. For example, β-cyclodextrin and its derivatives such as 6-0-α-glucosyl cyclomaltoheptaose, 6-0-α-maltosyl cyclomaltoheptalose and 6-0-tosyl cyclomaltoheptaose were found favorable for use in this invention.

The cyclodextrin substrate concentration is preferably higher than the Km value for the substrate of the cyclodextrinase.

The reaction conditions in acting the cyclodextrinase to cyclodextrins are not subject to any specific restrictions provided that the pH and temperature used for the reaction fall within the range where said cyclodextrinase can perform its planned action. The preferred pH range is 7.0–8.0 and the preferred temperature range is 35°–45° C.

If necessary, a useful substance or substances such as an organic solvent may be added to the reaction mixture. The reaction time depends on stability of the reaction product, but it is preferably within the range from about 30 minutes to about 48 hours. The enzyme feed is not specifically defined, but it is so selected that the yield of the reaction product will be maximized in the set reaction time. The enzyme may be properly supplied as desired in the course of the reaction. It is advisable that the reaction be terminated by an acid or heat treatment at a point when the yield of the reaction product is maximized.

From the maltooligosaccharide-containing reaction solution thus obtained, the desired maltooligosaccharide is extracted. Any ordinary method for separating oligosaccharides can be used, but in the case of the preparation process of the present invention, it is possible to easily obtain a high-purity maltooligosaccharide solution by removing unreacted cyclodextrin from the reaction solution. Removal of unreacted cyclodextrin from the reaction solution can be effected by known methods such as cooling, addition of an organic solvent, treatment with a cyclodextrin adsorption column, etc.

The present invention will hereinafter be described in further detail by showing the examples thereof.

EXAMPLES 100 ml of a liquid medium (using tap water, pH 7.0) containing 1% of β-cyclodextrin, 1% of peptone, 0.5% of NaCl and 0.1% of yeast extract was put into a 500-ml Sakaguchi's flask and sterilized by heating at 120° C., for 20 minutes. A platinum loopful of stock slant of *Bacillus sphaericus* E-244 strain (FERM BP-2458) was inoculated into said medium and subjected to shaking culture at 30° C. for one day. 50 ml of the resulting liquid culture was inoculated into 2,000 ml of a medium prepared with the same composition and sterilized in the same way as stated above, said medium being contained in a 3,000 ml minijar, and subjected to 2-day spinner culture under the conditions of 30° C., 1 vvm and 350 r.p.m. The liquid culture thus obtained was centrifuged at 8,000 r.p.m. for 20 minutes to separate the bacterial cells. The collected cells were suspended in 500 ml of a 10 mM phosphate buffer solution (pH 7.0) containing 2% of Triton X-100 and the suspension was stirred at 25° C. for one day. This suspension was further centrifuged at 12,000 r.p.m. for 20 minutes to remove the residual cells, and the supernatant was dialyzed against a 10 mM phosphate buffer solution (pH 7.0) for 16 hours. The dialyzate was centrifuged at 12,000 r.p.m. for 20 minutes to remove the insolubles, and the supernatant was collected to obtain a crude enzyme liquid (1).

Figure 1:
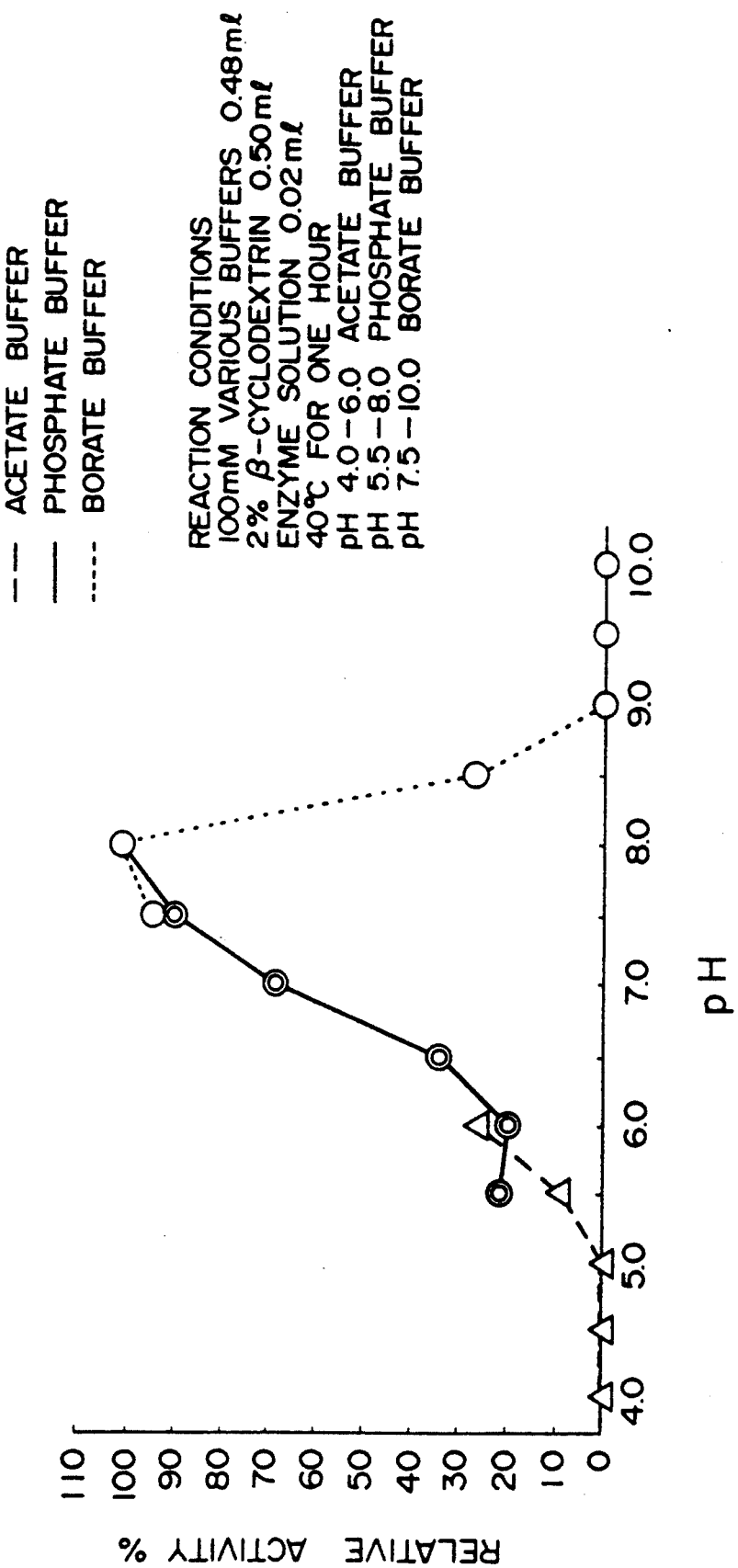
FIG. 1 is a graph showing the optimum pH range for the enzyme of the present invention.
Figure 2:
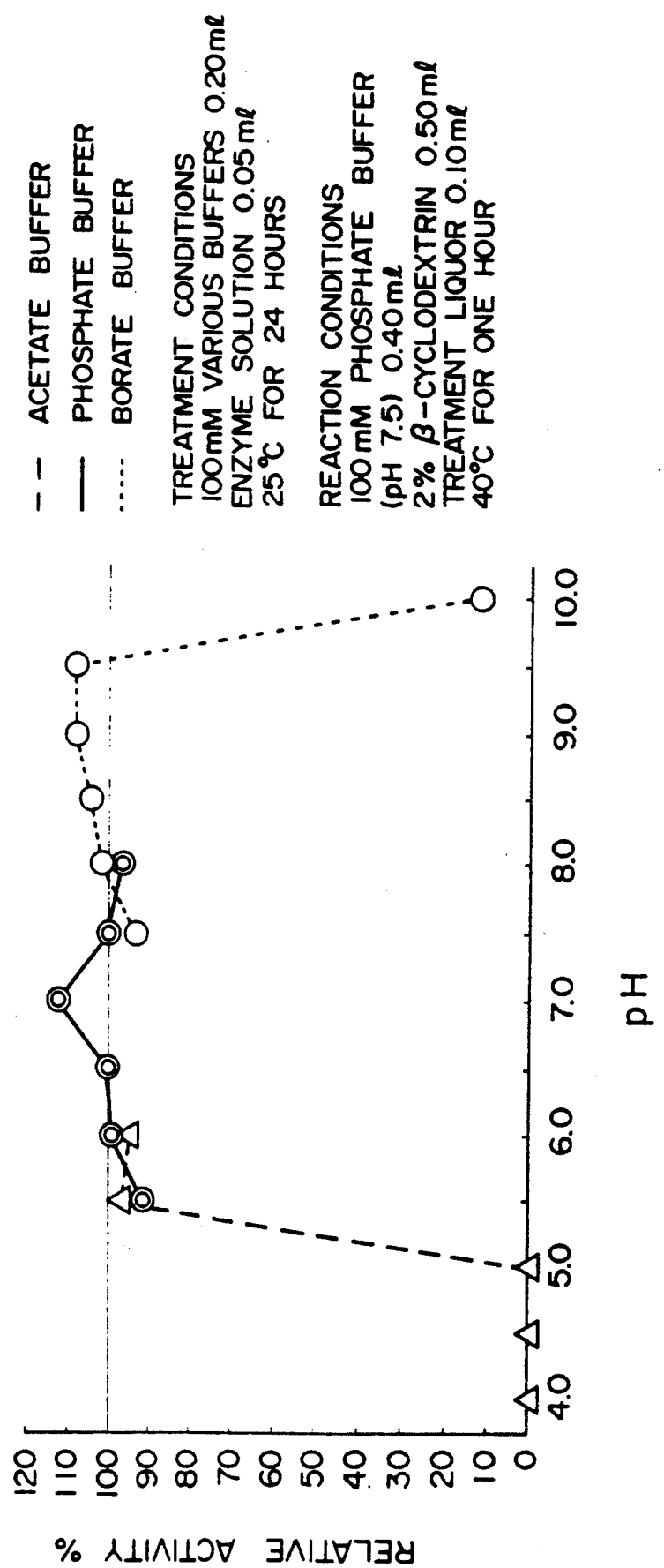
FIG. 2 is a graph showing the stability pH range for the present enzyme.
Figure 3:
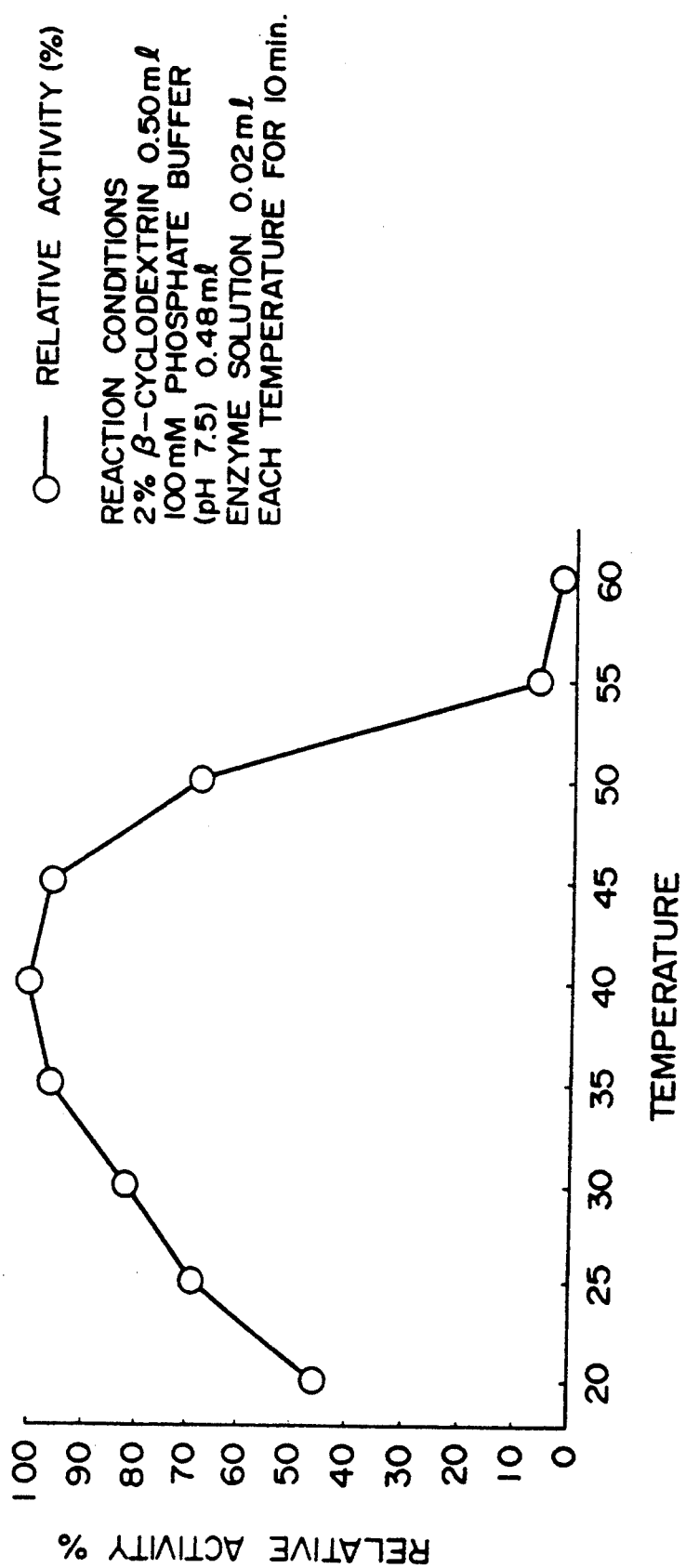
FIG. 3 is a graph showing the working temperatures for the present enzyme.
Figure 4:
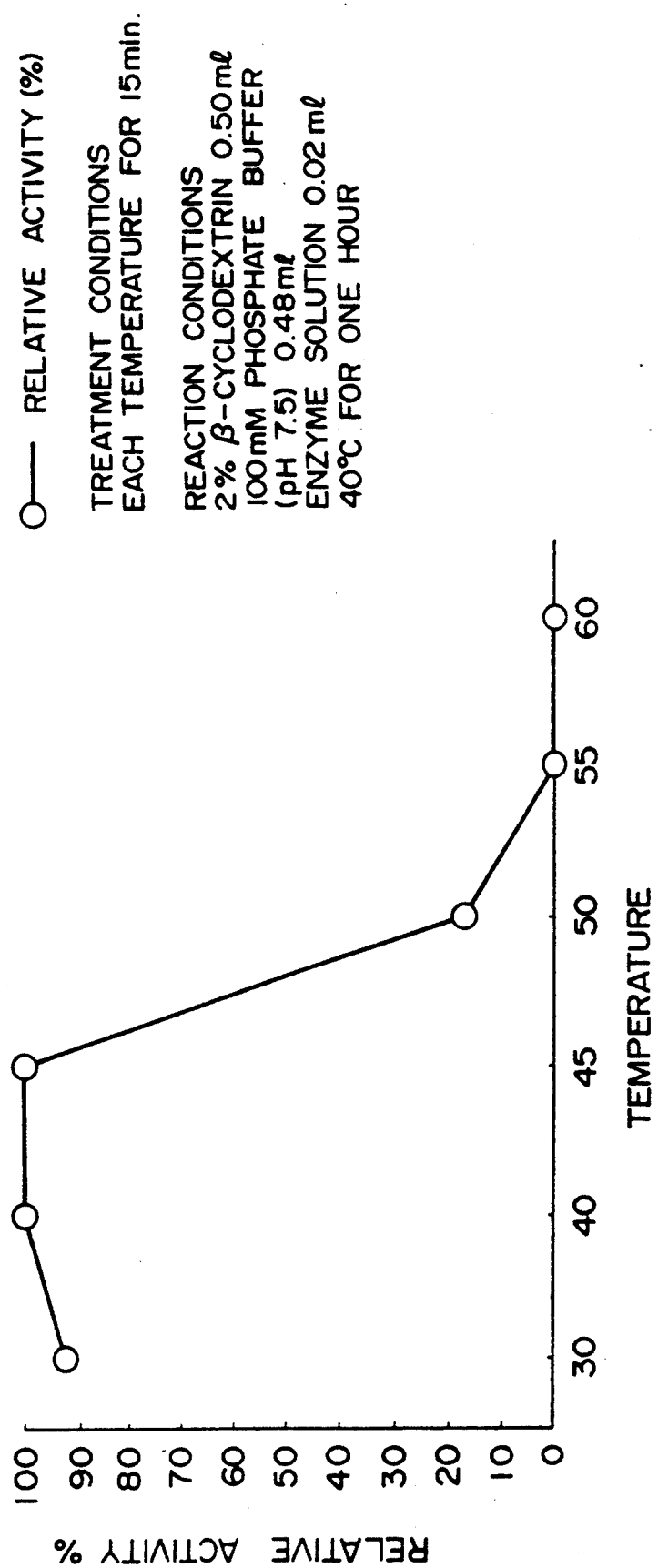
FIG. 4 is a graph showing the course of inactivation of the present enzyme according to temperature.
Figure 5:
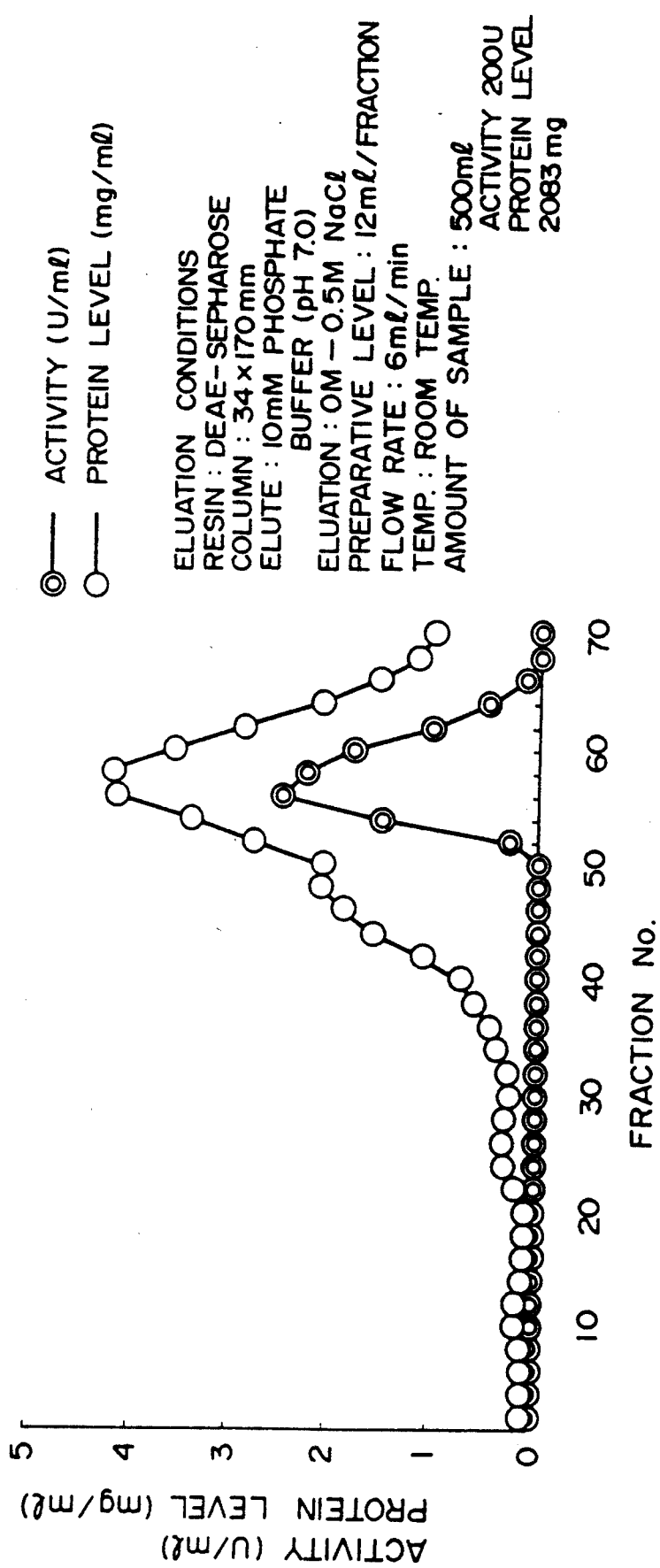
FIG. 5 is a graphic representation of the results of column chromatography of the present enzyme using DEAE Sepharose.

About 500 ml of said crude enzyme liquid (1) (overall activity: 200 units; specific activity: 0.1; pH: 7.0) was passed through a column (34×170 mm) packed with DEAE Sepharose equilibrated with a 10 mM phosphate buffer solution (pH 7.0), causing adsorption of the present enzyme on the column, and this column was subjected to gradient elution with 0–0.5M NaCl. An elution pattern of said DEAE Sepharose column chromatography is shown in FIG. 5. The active fractions were collected to obtain 105 ml of a crude enzyme liquid (2) (overall activity: 145 units; specific activity: 0.58; yield: 72.5%).

Figure 6:
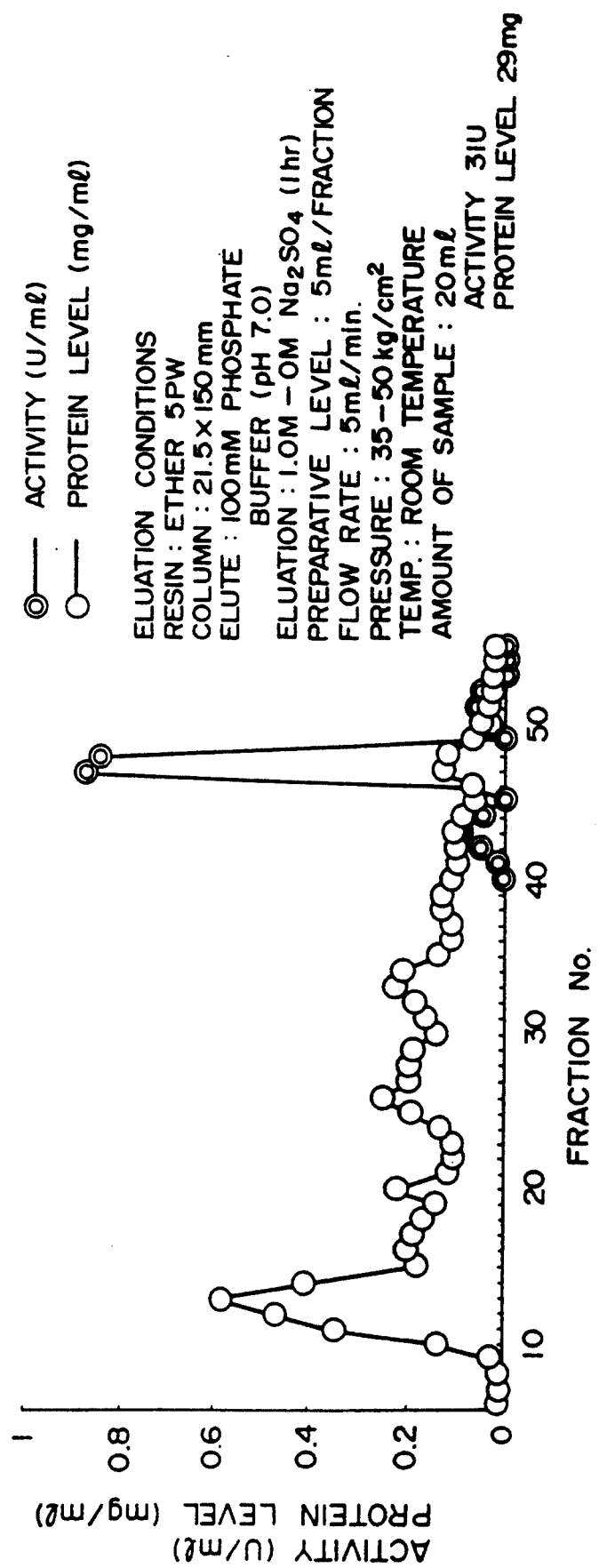
FIG. 6 is a graphic representation of the results of HPLC of the present enzyme using TSK gel ether 5 PW.

This crude enzyme liquid (2) was passed through a column (21.5×150 mm) packed with ether 5 PW equilibrated with a 100 mM phosphate buffer solution (pH 7.0) containing 1M sodium sulfate, where by the column was adsorbed with the present enzyme and subjected to gradient elution with 1–0M sodium sulfate. The resultant elution pattern is shown in FIG. 6. The active fractions were collected to obtain 50 ml of a crude enzyme liquid (3) (overall activity: 72 units; specific activity: 2.93; yield: 36%).

Figure 7:
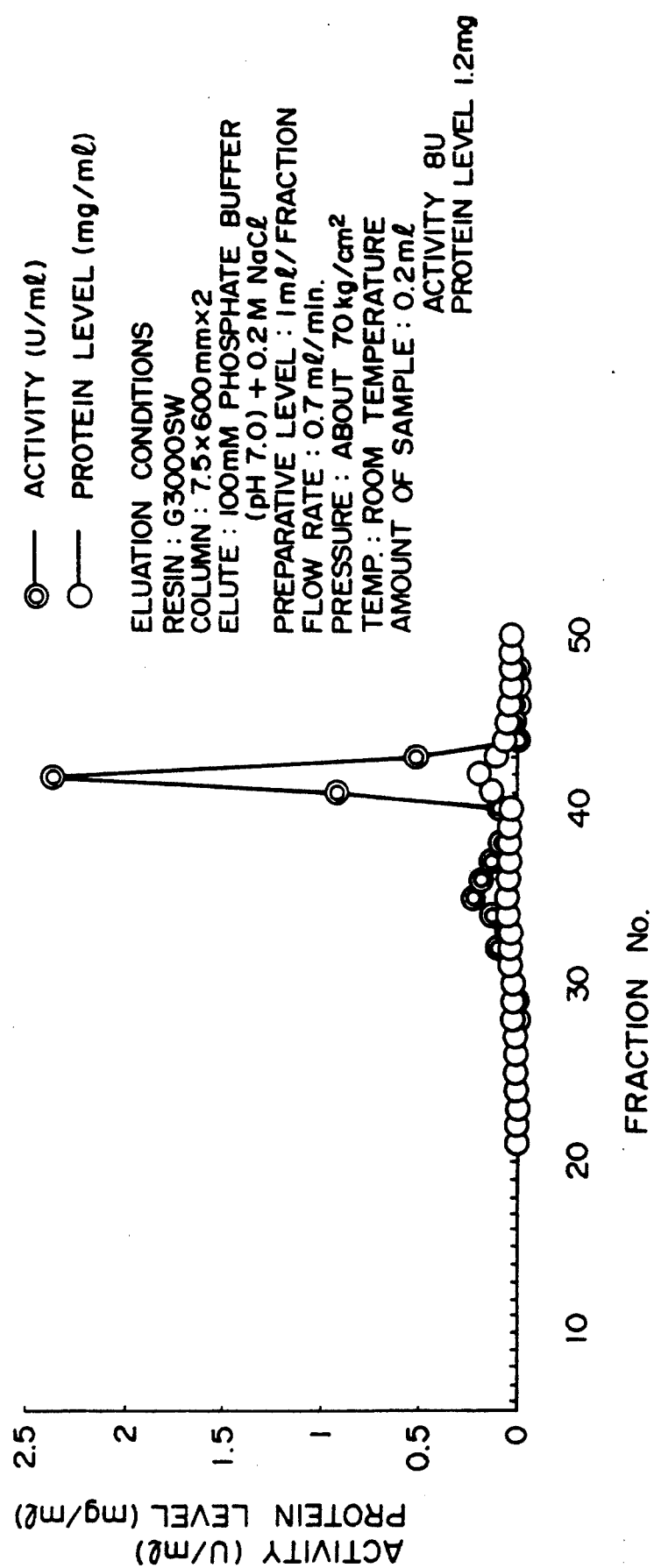
FIG. 7 is a graphic representation of the results of HPLC of the present enzyme using TSK gel G3000SW.
Figure 8:
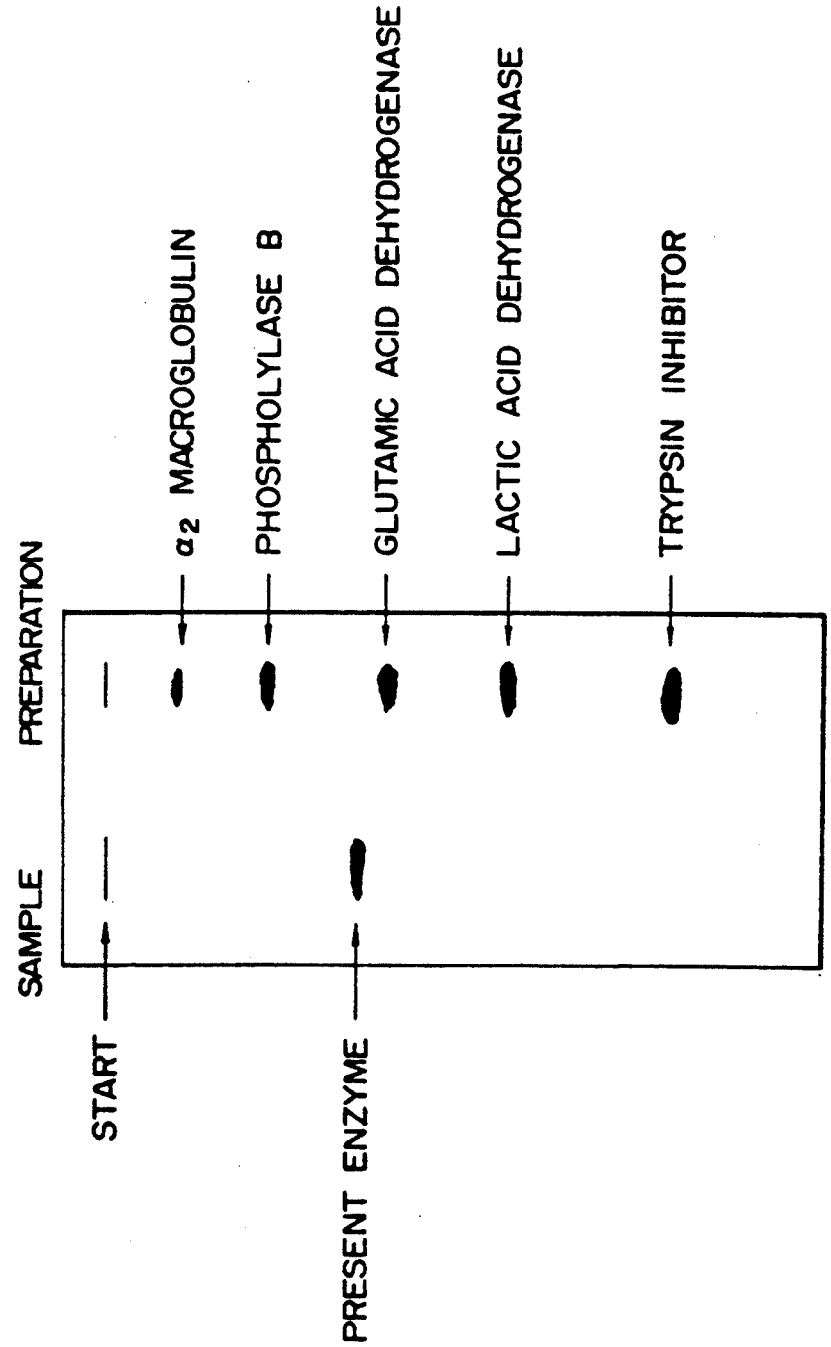
FIG. 8 is a drawing showing the results of SDS PAGE of the present enzyme.

This crude enzyme liquid (3) was ultra-concentrated to 1.5 ml by using a collodion bag, and 0.2 ml thereof was subjected to gel filtration using TSK gel G3000SW and then eluted with a 100 mM phosphate buffer solution (pH 7.0) containing 0.2M NaCl. The elution pattern is shown in FIG. 7. The active fractions were collected to obtain 1.4 ml of a purified enzyme liquid (overall activity: 2.2 units; protein content: 0.24 mg; specific activity: 9.17; yield: 1%). The enzyme thus obtained was of monotype in terms of SDS PAGE (see FIG. 8).

Figure 9:
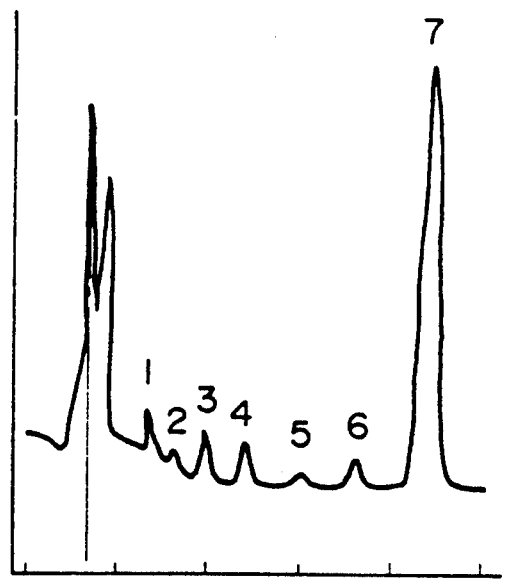
FIG. 9 is a chart pattern showing the result of analysis of the freeze-dried product of ODS column-passed solution by HPLC using TSK gel Amide 80.
Figure 10:
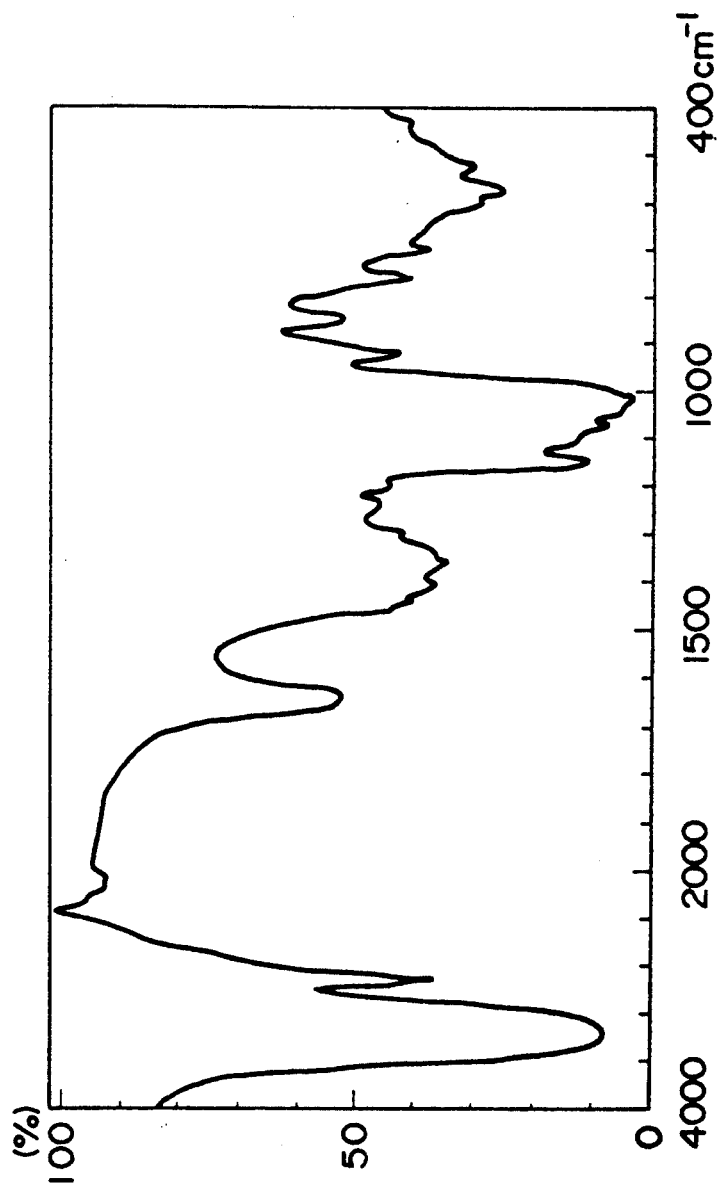
FIG. 10 is an IR analysis pattern of the freeze-dried product of the maltoheptaose fraction.

10 g of β-cyclodextrin were dissolved in 1,000 ml of a 100 mM phosphate buffer solution (pH 7.0), followed by addition of about 5 units of the crude enzyme liquid according to the present invention and 30-hour reaction at 40° C. to obtain a reaction solution. Hydrochloric acid was added to this reaction solution to make its pH about 2.0, at which the reaction was terminated. Then the reaction solution was neutralized with an NaOH solution and passed through an octadecylated silica gel (ODS) column to have the unreacted β-cyclodextrin adsorbed on the column, and the passed liquid fraction was freeze-dried in the usual way to obtain about 7 g of crude maltoheptaose powder. The result of analysis of this powder by HPLC using a TSK gel Amide 80 column (a packed column for partition/adsorption chromatography, mfd. by TOSO CORP ) is shown in FIG. 9. The ratio of maltoheptaose in the crude maltooligosaccharide was about 80%. Further, a maltoheptaose fraction was separated from said powder and purified by the conventional methods, and the freeze-dried maltoheptaose fraction powder was subjected to an IR spectral analysis The result is shown in FIG. 10. The analysis pattern of the maltoheptaose fraction was identical with that of standard preparation of maltoheptaose.

EFFECT OF THE INVENTION

In accordance with this invention, it is possible to obtain high-purity maltooligosaccharides by very simple operations at high efficiency. The present invention is thus of notably high industrial significance.

What is claimed is:

1. A process for producing maltooligosaccharides which comprises catalytically acting a cyclodextrinase enzyme (EC 3.2.1.54) having the following physico-chemical characteristics on cyclodextrins
   wherein the enzyme cleaves cyclodextrins to produce maltooligosaccharides corresponding to the polymerization degree of glucose of the cyclodextrins;
   the hydrolysis rate or affinity of said enzyme for cyclodextrins being higher than that of polysaccharides or linear maltooligosaccharides with the same polymerization degree of glucose as cylodextrins;
   when α-cyclodextrin is the substrate, $Km=0.71$;
   when γcyclodextrin is the substrate, $Kn=1.43$; and
   when β-cyclodextrin is used as a substrate, $Km=0.38$, the optimum pH of said enzyme is around 8.0 and the stable pH range is 5.5–9.5;
   the working temperature of the enzyme is around 40° C.;
   the enzyme is substantially inactivated by a treatment at a temperature of 50° C. or more for a period of 15 minutes;
   the enzyme is inhibited by at least 90% by $Hg^{2+}$, $Cu^{2+}$, $Zn^{2+}$, $Ni^{2+}$, and $Fe^{2+}$ and activated 10–30% by $Ca^{2+}$ and $Mg^{2+}$; and
   the molecular weight of the enzyme is 144,000 when measured according to gel filtration method and 72,000 when measured according to SDS PAGE method.

* * * * *